United States Patent [19]

Rouillard et al.

[11] Patent Number: 5,958,421
[45] Date of Patent: Sep. 28, 1999

[54] COSMETIC OR PHARMACEUTICAL COMPOSITION CONTAINING AN ANDIROBA EXTRACT

[75] Inventors: Françoise Rouillard, Longjumeau; Juliette Crepin, Paris; Gaëlle Saintigny, Paris, all of France

[73] Assignee: Laboratoires de Biologie Vegetale Yves Rocher, La Gacilly, France

[21] Appl. No.: 09/059,339

[22] Filed: Apr. 14, 1998

[30] Foreign Application Priority Data

Apr. 14, 1997 [FR] France .................................. 97 04550

[51] Int. Cl.$^6$ ........................... A61K 35/78; A61K 9/06; C11B 1/08
[52] U.S. Cl. ................ 424/195.1; 424/401; 514/783; 554/9
[58] Field of Search ............... 424/195.1, 401; 554/9; 514/783

[56] References Cited

U.S. PATENT DOCUMENTS 4,898,694  2/1990  Schwartz et al. .................... 540/94

OTHER PUBLICATIONS

Matthias L.A. Hammer et al., "Tapping an Amazônian Plethora: Four Medicinal Plants of Marajó Island, Pará (Brazil)", Journal of Ethno–Pharmacology, 40, Jun. 1993 pp. 53–75.

Derwent abstract, accession #88–213108.Gimenes, J.Q. Patent #BR 8605739. (Jun. 28, 1988).

Derwent abstract AN 94–008068. De Castro, patent #BR 9302006. (Sep. 28, 1993).

Cappiapuoti, et al. Canadian Journal of Microbiology 26(8), pp. 863–873. (Aug. 1980).

*Primary Examiner*—Kathleen K. Fonda
*Attorney, Agent, or Firm*—Young & Thompson

[57] ABSTRACT

The subject of the invention is the use of a lipid extract of Andiroba for the inhibition of glucose-6-phosphate dehydrogenase and its application to the inhibition of adipocyte differentiation.

9 Claims, 1 Drawing Sheet

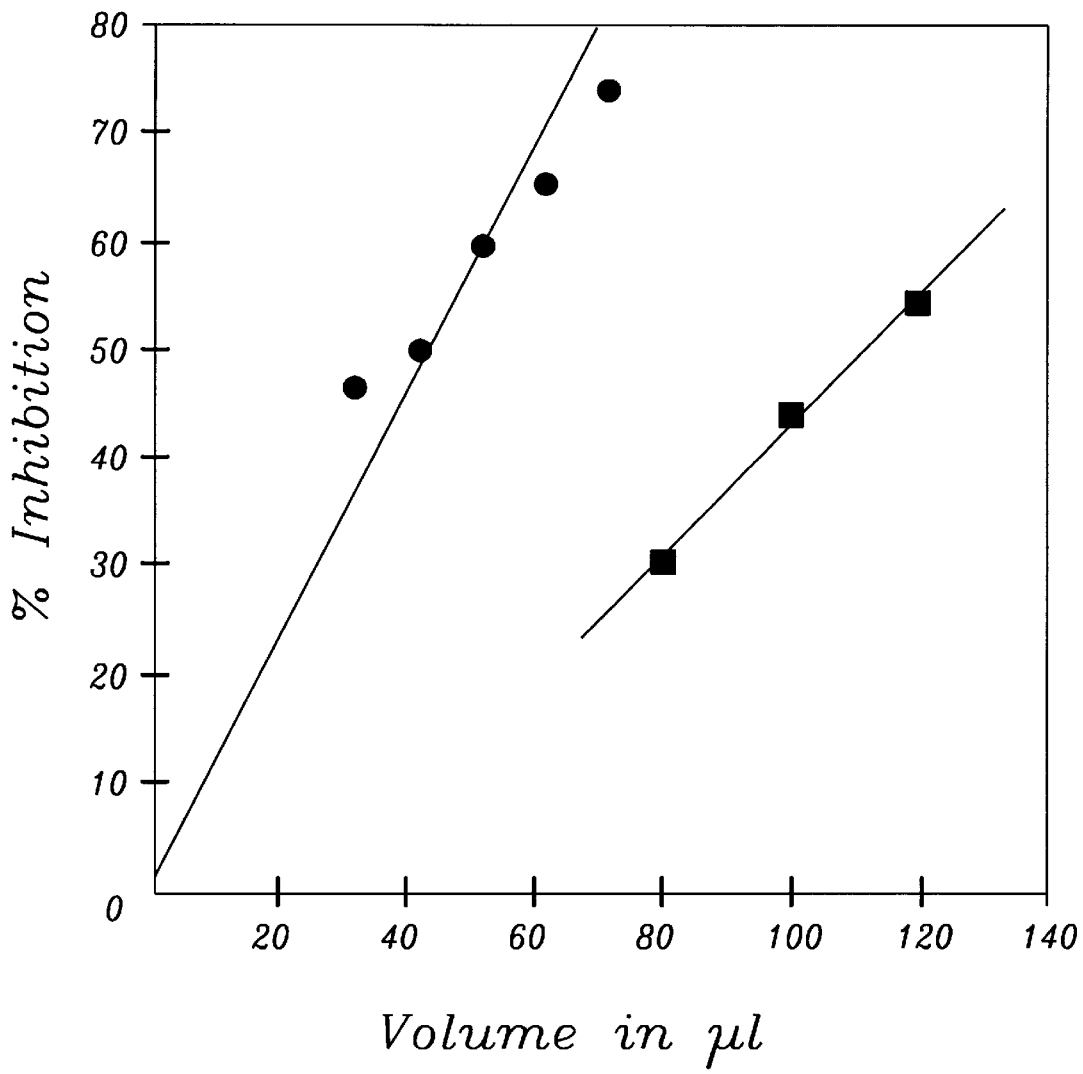

COSMETIC OR PHARMACEUTICAL COMPOSITION CONTAINING AN ANDIROBA EXTRACT

FIELD OF THE INVENTION

The invention relates to the cosmetic and pharmaceutical field, in particular to the treatment of cellulite.

The subject of the invention is more particularly a lipid extract of Andiroba for the treatment of cellulite.

BACKGROUND OF THE INVENTION

Andiroba (*Carapa guianensis* Aubl.) is a tree which belongs to the Meliaceae family. Originating from the Amazonian tropical forest, it can grow up to 25 meters, the trunk ends with a large foliage of leaves and branches, its fruits are large capsules containing 7 to 8 seeds of varying shapes.

The seeds of Andiroba contain a stone which represents 72 to 74% of the weight of the seed and which is rich in fat (of the order of 60–66%).

The lipid extract which can be obtained from these stones is traditionally used externally for its anti-inflammatory properties to soothe muscle and rheumatic pains, to treat insect bites or to tone up the hair and to get rid of lice. It is also used as a disinfectant or a cicatrisant for the skin. It is a general tonic by the internal route.

SUMMARY OF THE INVENTION

The authors of the present invention have demonstrated that the lipid extract of Andiroba possesses an inhibitory effect on glucose-6-phosphate dehydrogenase and, moreover, an inhibitory effect on adipocyte conversion.

The subject of the invention is thus the use of a lipid extract of Andiroba for the inhibition of glucose-6-phosphate dehydrogenase (G6PDH).

The subject of the invention is also the use of a lipid extract of the invention in order to obtain an inhibitory effect on adipocyte conversion.

By virtue of this effect on adipocyte conversion, the lipid extract of Andiroba according to the invention finds particularly advantageous applications for uses in a cosmetic composition or for the preparation of a pharmaceutical composition intended for regulating the mechanisms involved in cellulite so as to obtain an anticellulite effect.

Treatment of cellulite for the purposes of the present invention is understood to mean an essentially preventive treatment or a treatment intended to limit the progression of an established cellulite.

Indeed, the oily extract of Andiroba has practically no action on established cellulite, but acts on the inhibition of the differentiation of preadipocytes to adipocytes, therefore limiting the possibility of cellulite appearing.

At the heart of the metabolism of fats, under the epidermis, is the adipose tissue, which represents 15 to 20% of the body weight. The adipose tissue consists of a connective matrix which contains the adipocytes (the energy regulators, via the triglycerides) and specialized fibroblasts or preadipocytes.

While the preadipocytes, precursors of the adipocytes, have an elongated morphology characteristic of the fibroblasts, the adipocytes, at the end of their differentiation, are spherical cells whose intercellular space is filled with a large vesicle filled with triglycerides. The differentiation phenomenon is under the control of hormonal factors, growth factors and prostaglandins.

In the field of the invention, that is to say the treatment of cellulite, the inventors had a novel approach to slimness which consisted in controlling the phenomenon of differentiation of the preadipocytes into mature adipocytes.

One of the key enzymes in this differentiation is glucose-6-phosphate dehydrogenase which regulates the pentose pathway and is distributed in different body tissues such as: the liver, the mammary glands and the adipose tissue. It is cytoplasmic and active in the dimeric form. It catalyzes, in the presence of $NADP^+$, the oxidation of $\beta$D-glucose-6-phosphate to 6-phosphoglucopyrano-1,5-lactone and NADPH. The reaction is thermodynamically reversible, but it is made irreversible by the extremely rapid hydrolysis of the 6-phosphoglucopyrano-1,5-lactone, at pH>6.4.

In the adipose tissue, the enzyme in question thus makes it possible to generate: NADPH, the primary source of reducing power in the synthesis of fatty acids and of ribose 5-phosphate, the source of ribose for the biosynthesis of metabolites such as RNA, ATP and Coenzyme A.

The Andiroba extract according to the invention is obtained from the stones of Capara guianensis extracted from the nuts.

The principal constituents currently identified in this lipid extract are:

meliacines and oxygenated terpenes similar to quassinoids;

fatty acids: palmitic acid (31%), stearic acid (7%), arachidic acid (2%), hexadecenoic acid (1%), oleic acid (49.3%), linoleic acid (9%) and linolenic acid (0.7%).

The lipid extracts of Andiroba can be obtained by a treatment at high temperature after reducing the stones to a paste, and then passing through a press. The extract obtained in this case is a viscous liquid; it is decanted and optionally filtered.

Another possibility is to extract the oily fraction from the crushed stone using an apolar solvent, of the hexane type, the proportions of solvent relative to the raw material preferably being from 1 to 1.25 liters per kilo of material. The extraction is advantageously carried out with the aid of a solvent heated up to a temperature of less than 60° C., while controlling the flow rate of the solvent and the number of successive washes. The extract obtained in this case is distilled so as to separate the lipid fraction from the solvent which served for its extraction.

Novel technologies known to a person skilled in the art, such as for example the use of supercritical gas can also be used to obtain the lipid extract of Andiroba.

The extracts obtained according to the invention may contain 0.05% of butylhydroxtoluene, by weight, as antioxidant.

The subject of the invention is also a method for the cosmetic or pharmaceutical treatment of cellulite, characterized in that a lipid extract of Andiroba, optionally combined with a cosmetic or pharmacological vehicle, is applied to the area to be treated.

BRIEF DESCRIPTION OF THE DRAWINGS

The single FIGURE is a graphical representation of the lipid extract of example 1 (squares), and of palmitoyl CoA (circles) expressed as the percentage of inhibition with respect to the volume of either the extract or palmitoyl CoA.

DETAILED DESCRIPTION OF THE INVENTION

Examples of demonstration of the properties of the lipid extract of Andiroba of the invention will be described below.

EXAMPLE 1

I. Demonstration in vitro of the inhibitory effect of glucose-6-phosphate dehydrogenase An in vitro test was developed using a commercialized G6PDH isolated from baker's yeast. This colorimetric technique makes it possible to identify and to select potential inhibitors of the differentiation of preadipocytes to adipocytes.

The enzyme (G6PDH) is brought into contact with D-glucose-6-phosphate and nicotinamide adenine dinucleotide phosphate ($NADP^+$). The enzymatic activity is measured by the reduction of $NADP^+$ to NADPH and by the oxidation of the D-glucose-6-phosphate to 6-phosphoglucopyrano-1,5-lactone. The reduced nicotinamide adenine phosphate (NADPH) then reacts with a phenazine methosulphate/thiazolyl blue (PMS/MTT) system to give a colored complex which absorbs at 560 nm (Richard W. Geisler, Alyn M. McClure and Robert J. Hansen, Biochimica and Biophysica Acta, 327, 1973, 1–10).

For each kinetics, a mean rate is measured.

The ratio of the mean rates X to the mean rate of the control activity, multiplied by 100, makes it possible to calculate a percentage of inhibition.

The volume of the active ingredient tested, which is necessary to obtain 50% inhibition is determined graphically.

The inhibitory effect of an active ingredient is defined relative to a reference inhibitor: palmitoyl CoA.

$$\text{Inhibitory effect} (A.U) = \frac{X \, \mu l \text{ palmitory CoA} \times [\text{palmitoyl CoA}]}{y \, \mu l \text{ solution } X \times [\text{solution } X]} \times 100$$

The lipid extract of Andiroba obtained according to one of the processes described above is solubilized in dimethyl sulphoxide (DMSO) and tested in vitro on the activity of glucose-6-phosphate dehydrogenase.

The results are illustrated in the accompanying single FIGURE, which represents the inhibitory effect of the lipid extract of Andiroba (squares), and of palmitoyl CoA (circles) expressed as the percentage of inhibition with respect to the volume of either the extract or palmitoyl CoA.

The inhibitory effect is 1.9 to 2.8 (Arbitrary Units), that is to say that the lipid extract of Andiroba is 30 to 50 times less active than palmitoyl CoA. It possesses, nevertheless, an advantageous inhibitory potential which makes it possible to envisage its use as inhibitor of the differentiation of preadipocytes to adipocytes.

EXAMPLE 2

II. Demonstration in vitro of the inhibitory effect on adipocyte differentiation The study is carried out on a 3T3L1 cell line which, under certain culture conditions, is capable of becoming differentiated, accumulating vesicles containing triglycerides. The stage of adipocyte differentiation is proportional to the activity of G3PDH, which is the marker specific for this differentiation.

The cells are first brought to confluence using a proliferation medium (DMEM+10% fetal calf serum). Next, cell differentiation is induced by incorporating insulin, dexamethasone and isobutyl methyl xanthine into this culture medium. The active agent to be tested is introduced at the time of differentiation. Its effect is proportional to the quantity of the cellular G3PDH activity, expressed per mg of protein.

The G3PDH activity is determined in vitro on the supernatant of a ground cellular product: G3PDH in the presence of β-nicotinamide adenine dinucleotide, reduced form ($NADH_2$), converts dihydroxyacetone phosphate (DHAP) to glycerol phosphate. The disappearance of $NADH_2$ is linked to the GP3PDH activity and is monitored in a spectrophotometer at 340 nm.

If the lipid extract of Andiroba, solubilized at 0.02% in DMSO, is introduced at the time of induction of differentiation, the resulting expression of the G3PDH activity in the cellular supernatant is inhibited by 25 to 50% compared with the expression of the G3PDH activity in the control cellular supernatant (without active agent).

The lipid extracts of Andiroba obtained according to the invention, inhibitors of G6PDH and, moreover, inhibitors of adipocyte conversion, can therefore be used in care cosmetics or in pharmacy to help the regulation of the mechanisms for controlling cellulite.

Their mode of administration is by the topical route.

The Andiroba extracts according to the invention can be used as they are, vectorized, microencapsulated, in combination with a mixture of excipients such as: vegetable oils, mineral oils, vegetable or mineral waxes, silicones, alcohols and fatty acids, surfactants and the like, or in combination with other plant extracts or molecules of natural origin.

The compositions cover all the cosmetic or pharmaceutical forms, of the following types: simple O/W or W/O emulsions, multiple emulsions or microemulsions, aqueous or lipophilic gels, oils, sprays, sticks and the like.

The following examples of composition containing a lipid extract of Andiroba as active ingredient illustrate the present invention.

The percentages are given by weight.

EXAMPLE 3

Composition in the form of an aqueous gel

| | |
|---|---|
| Polyacrylic acid | 0.5–1.2% |
| Xanthan gum | 0.3–0.5% |
| Water | qs 100% |
| Humectants | 5.0–10.0% |
| Lipid extract of Andiroba | 0.01–5.0% |
| Other extracts | 0–20.0% |
| Ethanol | 5.0–30.0% |
| Perfume | 0.2% |
| NaOH | 0.1–0.6% |
| Colorant | 0.05–0.5% |

EXAMPLE 4

Composition in the form of an O/W emulsion (milk or cream)

| | |
|---|---|
| Water | qs 100% |
| Preservatives | qs |
| Humectants | 5.0–10.0% |
| Xanthan gum | 0.1–0.3% |
| Acrylic/acrylate copolymer | 0.1–0.5% |
| Stearic acid 10 EO | 3.0% |
| Sorbitan stearate | 2.0% |
| Sorbitan stearate 20 EO | 3.0% |
| Cetylstearyl alcohol | 0–1.5% |
| Lipid extract of Andiroba | 0.5–25.0% |
| Tocopherol acetate | 0.1% |
| Silicones | 2.0–7.0% |
| Polyacrylamide gel | 0–2.0% |
| Other extracts | 0–20.0% |
| Perfume | 0.3% |

EXAMPLE 5

Composition in the form of a lotion

| | |
|---|---|
| Water | qs 100% |
| Humectants | 3.0–10.0% |
| Preservatives | qs |
| Alcohol | 1.0–7.0% |
| Solubilizer | 0–15.0% |
| Lipid extract of Andiroba | 0.01–10.0% |
| Other extracts | 0–20.0% |
| Perfume | 0.05–0.2% |

EXAMPLE 6

Composition in the form of a body oil

| | |
|---|---|
| Mineral oil | qs 100% |
| Tocopherol acetate | 0.1% |
| Lipid extract of Andiroba | 1.0–25.0% |
| Vegetable oil | 1.0–25.0% |
| Extracts | 0–10.0% |
| Perfume | 0.3–1.0% |

EXAMPLE 7

Composition in the form of a stick

| | |
|---|---|
| Castor oil | qs 100% |
| Vegetable waxes | 5.0–15.0% |
| Other waxes | 10.0–20.0% |
| Lipid extract of Andiroba | 1.0–25.0% |
| Tocopherol acetate | 0.1% |
| Petroleum jelly | 5.0–10.0% |
| Shea butter | 5.0% |
| Perfume | 0.3% |

The lipid extracts of Andiroba can be used as a cosmetic or for pharmaceutical purposes in amounts of 0.01 to 100%.

Preferably, the compositions according to the invention comprise from 0.01% to 25% by weight of lipid extract of Andiroba.

We claim:

1. A method for inhibiting glucose 6-phosphate dehydrogenase in adipocytes, which comprises:
    applying to a skin a cosmetic or pharmaceutical composition comprising 0.01–100% by weight of a lipid extract of Andiroba.

2. The method according to claim 1, wherein the lipid extract is obtained from *Carapa guinanensis* stones.

3. The method according to claim 1, wherein the lipid extract of Andiroba is obtained by reducing *Carapa guinanensis* stones to a paste, heating said paste, passing said heated paste through a press, decanting the pressed paste, and optionally filtering the paste.

4. The method according to claim 1, wherein the lipid extract is obtained by extracting an oily fraction from crushed stones of *Carapa guinanensis* with an apolar solvent by heating at a temperature of less than 60° C., followed by removal of the solvent and isolation of the lipid extract.

5. The method according to claim 1, which comprises applying to the skin a cosmetic or pharmaceutical composition comprising from 0.01 to 100%, by weight of the lipid extract of Andiroba.

6. The method according to claim 1, which comprises applying to the skin a cosmetic or pharmaceutical composition comprising 0.01 to 25% by weight of the lipid extract of Andiroba, and a cosmetic or pharmaceutical vehicle.

7. A method of inhibiting differentiation of preadipocyte into adipocyte, which comprises:
    applying to a skin a cosmetic or pharmaceutical composition comprising 0.01–100% by weight of a lipid extract of Andiroba in order to limit progression of cellulite.

8. A method for cosmetic treatment of cellulite, which comprises:
    applying to the skin a cosmetic composition comprising greater than or equal to 0.01% by weight of a lipid extract of Andiroba, combined with a cosmetically acceptable vehicle.

9. A method for therapeutic treatment of cellulite, which comprises: applying to the skin a pharmaceutical composition comprising greater than or equal to 0.01% by weight of a lipid extract of Andiroba, combined with a pharmaceutically acceptable vehicle.

* * * * *